United States Patent [19]

Turner et al.

[11] Patent Number: 4,973,743

[45] Date of Patent: Nov. 27, 1990

[54] PROCESS FOR THE PRODUCTION OF POLYBASIC ACID ESTERS WITH RECOVERY OF BORON TRIFLUORIDE

[75] Inventors: Stephen W. Turner, Hamilton, Ohio; Charles W. Blewett, Lakeside Park, Ky.

[73] Assignee: Henkel Corporation, Ambler, Pa.

[21] Appl. No.: 428,093

[22] Filed: Oct. 27, 1989

[51] Int. Cl.$^5$ .............................................. C07C 67/465
[52] U.S. Cl. .................................... 560/202; 502/31; 502/56; 502/203; 560/190
[58] Field of Search .................. 560/190, 202; 502/31, 502/56, 203

[56] References Cited

U.S. PATENT DOCUMENTS 3,000,964  9/1961  Milligan .............................. 568/792
3,929,749  12/1975  Cooper et al. ...................... 502/32 X
4,017,548  4/1977  Petrille ................................ 568/792

OTHER PUBLICATIONS

Croston et al., *Journal of the American Oil Chemists' Society*, (Aug. 1952), pp. 331-333.
Ghodssi et al., *Bulletin de la SocieteChimique de France*, No. 4, (1970), pp. 1461-1466.

*Primary Examiner*—Werren B. Lone
*Assistant Examiner*—Vera C. Clarke
*Attorney, Agent, or Firm*—Ernest G. Szoke; Wayne C. Jaeschke; John E. Drach

[57] ABSTRACT

This invention provides a process for preparing an oligomer of at least one polyunsaturated aliphatic $C_{12-22}$ monocarboxylic acid ester in the presence of boron trifluoride resulting in a high yield or predominantly trimeric product which, upon hydrolysis, affords a high yield of polybasic, predominantly trimeric, acids. This invention further provides such a process with excellent recovery of the boron trifluoride.

14 Claims, No Drawings

PROCESS FOR THE PRODUCTION OF POLYBASIC ACID ESTERS WITH RECOVERY OF BORON TRIFLUORIDE

BACKGROUND OF THE INVENTION

1. Field of the Invention

This invention relates to a process for preparing oligomer of at least one polyunsaturated aliphatic $C_{12-22}$ monocarboxylic acid ester in the presence of boron trifluoride resulting in a high yield of predominantly trimeric product with excellent recovery of the boron trifluoride.

2. Description of the Related Art

The oligomerization of esters of unsaturated monocarboxylic acids in the presence of boron trifluoride ($BF_3$) to produce mixtures of dibasic acids, also known as dimer acids, and polybasic acids, also known as trimer or higher acids, is well known. For instance, Croston et al. "Polymerization of Drying Oils. VI. Catalytic Polymerization of Fatty Acids and Esters with Boron Trifluoride and Hydrogen Fluoride", Journal of the American Oil Chemists' Society, 331–333 (Aug., 1952) describes the polymerization of soybean fatty acids as well as their methyl esters in the presence of boron trifluoride. Typically, use of 2% $BF_3$ as a catalyst at 150°–200C. resulted in the polymerization of 50–60% of the methyl esters within one hour. $BF_3$ catalysis resulted in a low ratio of dimers to higher polymers, although the product distribution was not well-characterized.

Ghodssi et al. "Cationic Polymerization of Oleic Acid and its Derivatives. Study of Dimers", Bulletin de la Societe Chimique de France No. 4: 1461–1466 (1970) describes the synthesis of methyl cleate dimers, including higher polymeric by-products, by cationic polymerization of methyl oleate by bubbling $BF_3$ through the monomer at about 20°–30C. Molecular distillation gave two fractions which were characterized as the monomer (53.6 w/o) and dimers (18 w/o), as well as a residue (23.2 w/o) which was characterized as oligomers with a degree of oligomerization greater than 2. Here and throughout this application measurements given in percent mean weight percent (w/o) unless otherwise noted.

Dimer and trimer acids produced by oligomerization of unsaturated fatty acids (e.g., tall oil) have a variety of commerical and industrial uses. Dimer acids are used in solid and liquid polyamide resins, urethane resins, corrosion inhibitors, maintenance paints, varnishes, adhesives, soaps, polymer modifiers, oil additives, and lubricants. Trimer acids or their amine derivatives are particularly useful as a corrosion inhibitor/rust preventative in drilling mud formulations for the oil drilling industry, as a flexibilizing curing agent for epoxy resin coatings, and in soap-based lubricating greases. Most dimer and trimer acids sold commercially are actually mixtures of the two in which the named acid predominates. However, quite pure dimer and trimer acids are separable by molecular distillation and are available commercially. In fact, pure trimer acids are presently commercially obtained as by-products of the purification of dimer acids by molecular distillation. Unfortunately, the often limited demand for molecularly distilled dimer acids results in a limited production of the trimer acid by-product which is insufficient to satisfy the demand for it. Thus, in the past, a number of attempts have been made to produce trimer acid, instead of dimer acid, as the major reaction product. These prior art oligomerization reactions have involved a variety of catalysts, including modified montmorillonite clays, zeolites, peroxides or hydroperoxides (for free radical-initiated polymerization reactions), and strong acids such as p-toluenesulfonic acid. However, these catalysts produced insufficient yields of trimer acids and/or undesirable by-products.

Oligomerization of linoleic acid with 3–5% $BF_3$ is known to give a trimer acid product having a low saponification number (about 180) and acid value (about 160) resulting from formation of interesters, which are by-products resulting from the unwanted reaction between the carboxyl function and the alkenic function of the starting material. Further reaction over montmorilite clay to reduce the interester results in a trimer acid product of poor quality.

The use of boron trifluoride, a Lewis acid, as a Friedel-Crafts-type catalyst is well known. For instance, U.S. Pat. No. 3,000,964, issued to J. G. Milligan, describes a process using BF3 catalysis in the alkylation of phenols. U.S. Pat. No. 3,929,749, issued to T. A. Cooper and A. L. Logothetis and references cited therein, discusses the use of BF3 catalysis in the production of alternating copolymers of ethylene and alkyl acrylates. In the cationic polymerization of unsaturated carboxylic acids and esters to yield polybasic acid products, mentioned hereinabove, $BF_3$ is known to be advantageous because it catalyzes the reaction at low temperatures, thereby minimizing the degradative by-products which occur when catalysts requiring higher temperatures are utilized. In order to achieve desirable reaction rates, however, these syntheses require substantial, and often greater than stoichiometric, amounts of $BF_3$ due to initial complexation of the catalyst with starting material. Because $BF_3$ is relatively expensive, such processes are not economically practicable without the recovery and recycling of the $BF_3$.

$BF_3$ may be removed from the reaction mixture in several ways. Some techniques are degradative and therefore not of interest. For instance, steam stripping of an alkyl acrylate copolymer solution containing $BF_3$ complexed to the alkyl acrylate moiety allows isolation of uncomplexed copolymer but the resulting hydrolysis of the $BF_3$ precludes its recovery and recycling. However, a number of removal techniques are known which do not degrade the $BF_3$.

Pyrolysis removes BF3 by heating the reaction mixture to elevated temperatures and holding while the gaseous catalyst is evolved. However, such heating can cause undesirable degradation of the reaction product.

Several solvent stripping techniques for BF3 removal are also known. U.S. Pat. No. 3,929,749 describes a process wherein superheated solvent is passed into a pressurized heated reactor containing a BF3-complexed ethylene-alkyl acrylate copolymer solution and BF3-complexed alkyl acrylate. Using sufficient pressure to keep the solvent from volatilizing, the solution is heated sufficiently to dissociate the complexes and to liberate the $BF_3$. The whole mixture is then passed into a flash chamber, held at atmospheric or subatmospheric pressure, causing the $BF_3$ to flash off along with the solvent. In U.S. Pat. No. 3,000,984, process for removing BF3 from a phenol alkylation mixture is described. An inert paraffinic or aromatic hydrocarbon entrainer in which BF3 is sparingly soluble, having a boiling point within the range of 30°–200C. at atmospheric pressure, is added to the reaction mixture. In general, from 30–200 weight percent (w/o) entrainer (relative to reaction mixture weight) is required. The mixture is heated until the entrainer boils, the entrainer is condensed and reused, while the gaseous BF3 is removed and recycled by complexation with phenol starting material.

Similarly, U.S. Pat. No. 4,017,548, issued to D. G. Petrille describes another process for the recovery of BF$_3$ from a phenol alkylation mixture by solvent stripping. An inert alkane hydrocarbon with a boiling point within the range of 80°–125C. is continuously dissolved in the reaction mixture in an amount of 6–25 w/o, relative to the reaction mixture. The resulting mixture is continuously heated in incremental portions to 100°–130C., which causes the BF$_3$ phenolate complex to dissociate and the alkane to vaporize. The alkane vapors strip the BF$_3$ out of the reaction mixture, thereby liberating gaseous BF$_3$ which is recycled for use by complexation with the phenolic starting material. While effective in removing BF$_3$, such solvent stripping techniques have the disadvantage of requiring relatively large quantities of solvent, thereby increasing solvent and processing costs.

SUMMARY OF THE INVENTION

It is, therefore, a principal object of this invention to provide a process for preparing an oligomer of at least one polyunsaturated aliphatic $C_{12-22}$ monocarboxylic acid ester in the presence of boron trifluoride resulting in a high yield of predominantly trimeric product with excellent recovery of the boron trifluoride.

It is a further object of this invention to provide such a process wherein boron trifluoride is recovered with efficient use of solvent and handling equipment.

This invention is based on the discovery that, in a process for preparing oligomers of polyunsaturated fatty acid esters using BF$_3$ as a catalyst, the recovery yield of BF$_3$ by solvent refluxing generally significantly increases as the acid value (due to free carboxylic acid) of the ester starting material or feedstock decreases. The research leading up to this invention has been focused on optimizing the yield of a predominantly trimeric product of the BF$_3$ catalyzed oligomerization of polyunsaturated, $C_{12-22}$ monocarboxylic acid esters while also optimizing the recovery for reuse of the expensive BF$_3$ catalyst. Because the yield of the desired trimeric product generally increases with increasing acid value of the starting material or feedstock ester, a trend which inhibits efficient BF$_3$ recovery, it has been found that the acid value of the feedstock must be carefully balanced to optimize both the yield of trimeric product and the recovery yield of BF$_3$.

The process of the present invention enables preparation of an oligomer of at least one polyunsaturated aliphatic $C_{12-22}$ monocarboxylic acid ester in the presence of boron trifluoride, and for recovering the boron trifluoride in an efficient and effective manner by the steps of:

(a) reacting at least one said ester, having an acid value of about 0.01–10, at a reaction temperature and for a time sufficient to produce a predominantly trimeric reaction product;

(b) mixing an inert hydrocarbon having a boiling point of 50° C. or higher with said reaction product;

(c) heating the resulting mixture at a temperature causing said mixture to reflux, thereby releasing gaseous boron trifluoride; and (d) recovering at least the major portion of said boron trifluoride.

Further objects and the nature of the invention will be more clearly understood by reference to the following detailed description and appended claims.

DETAILED DESCRIPTION OF THE INVENTION

In accordance with the present invention, a process is provided for oligomerizing one or more polyunsaturated aliphatic $C_{12-22}$ monocarboxylic acid esters in the presence of boron trifluoride, whereby trimer production and recovery of the boron trifluoride are optimized. The term "polyunsaturated" is used within its usual chemical definition, that is, the term means containing two or more double bonds. The process of the invention comprises the steps of:

(a) reacting at least one polyunsaturated aliphatic $C_{12-22}$ monocarboxylic acid ester, having an acid value of about 0.01–10, at a reaction temperature and for a time sufficient to produce a predominantly trimeric reaction product;

(b) mixing an inert hydrocarbon having a boiling point of 50° C. or higher with the reaction product;

(c) heating the resulting mixture at a temperature causing said mixture to reflux, thereby releasing gaseous boron trifluoride; and (d) recovering at least the major portion of the boron trifluoride.

The present invention contemplates the use of at least one of a wide variety of polyunsaturated $C_{12-22}$ monocarboxylic acid esters as starting material or feedstock. The corresponding free acids are not used because, as will be discussed hereinbelow, the present invention requires the feedstock to have a low acid value. Also, the BF$_3$ catalyzed oligmerization of unsaturated free acids under the conditions of the present process results in the formation of undesirable interesters and lactones in unacceptable amounts in the reaction product mixture. The BF$_3$ catalyzed oligomerization of monounsaturated carboxylic acid esters under the conditions of the present process undesirably yields a predominantly mono meric reaction mixture and results in an unacceptably—low BF$_3$ recovery, thus, this class of esters is not used in the present process. The feedstock esters are readily synthesized from the appropriate carboxylic acid by known esterification procedures. These acids include the polyunsaturated linoleic and linolenic acids (both $C_{18}$). The use of various mixtures of esters as feedstocks is also contemplated by the present invention. Such mixtures may include monounsaturated esters as well as significant amounts of the desirable polyunsaturated esters, but preferably the esters in these mixtures are predominantly polyunsaturated. Contemplate feedstock mixtures include esterified mixtures of carboxylic acids derived from soybean oil (typically a mixture of about 10.5 w/o palmitic acid, 3.0 w/o stearic acid, 22.5 w/o oleic acid, 54.5 w/o linoleic acid, 8.5 w/o linolenic acid, and 1.0 w/o arachidonic acid), sunflower oil (typically a mixture of about 7.0 w/o palmitic acid, 3.3 w/o stearic acid, 14.3 w/o oleic acid, and 75.4 w/o linoleic acid), corn oil (typically a mixture of about 11.5 w/o palmitic acid, 2.0 w/o stearic acid, 26.5 w/o oleic acid, 59.0 w/o linoleic acid, and 1.0 w/o linolenic acid), cottonseed oil (a mixture of about 25.0 w/o palmitic acid, 17.0 w/o oleic acid, and 53.0 w/o linoleic acid and minor amounts of myristic, palmitoleic, and stearic acids), and tall oil (a mixture of about 59.5 w/o oleic acid and 37 w/o linoleic acid and minor amounts of stearic, arachidic, and arachidonic acids).

The $C_{1-20}$ alkyl esters of the carboxylic acids hereinabove described are preferably utilized as feedstock in the present process. Better yet, the methyl, ethyl, or propyl esters are used, and use of the methyl esters is most preferable.

A preferred group of feedstocks for the process of the invention are the esters derived from soybean oil, sunflower oil, corn oil, or cottonseed oil. The most preferred group of feedstocks are the methyl esters derived from this same group of oils.

The broad range of permissible acid values for the feedstock esters is about 0.01–10. Use of an acid value at the upper end of this range will result in the recovery of at least the major portion of the boron trifluoride used. Use of acid value above 10, however, will result in an unacceptably low recovery yield for the $BF_3$. A acid value of at least 0.01 is required of the feedstock ester because a small amount of a proton donor, here the free acid, is required as a cocatalyst in addition to the $BF_3$ to generate the active catalytic species in situ. To recover at least 85 w/o $BF_3$, the feedstock ester acid value should lie within the preferred range of 0.01–6. $BF_3$ recovery is essentially quantitative when the feedstock has an acid value within the more preferred range of 0.01–1.5, and better yet, within the most preferred range of 0.1–0.6.

Upon charging the reaction vessel with the desired quantity of feedstock ester, the ester is heated with stirring to the reaction temperature. The present process is conducted at a temperature and for a time sufficient to produce a predominantly trimeric reaction product. Preferably the present process is conducted at a reaction temperature in the range of about 0°–100C. The yield of trimer relative to the reaction product is a function of reaction temperature. Above about 100° C., the dimers become the predominant reaction product thereby decreasing the yield of the desired trimer product. It is well known that this result is due to the fact that in cationic polymerizations isomerization predominates over oligomerization at higher temperatures, leading to lower average product molecular weight. Below about 0° C., the process usually cannot be conducted efficiently because the reaction mixture becomes too viscous to stir. The process is more preferably conducted at about 15°–75C., and most preferably at about 20°–40°C.

An amount of gaseous $BF_3$ sufficient to effectively catalyze the oligomerization reaction is bubbled into the liquid feedstock at a partial pressure sufficient to ensure $BF_3$ saturation. Due to the well known facile complexation of $BF_3$ by the ester, $BF_3$ acts both as a reagent and a catalyst. Therefore at least a slight molar excess, but usually no more than about 110 mole percent, of $BF_3$ is used. The process is run for a time sufficient to maximize the production of trimeric product, usually 2–3h.

Following the oligomerization reaction, a hydrocarbon solvent having a boiling point of 50° C. or higher, and which is inert toward the reaction product, feedstock and $BF_3$ complexes thereof, is mixed with the reaction product. Preferably, the inert hydrocarbon is a $C_{6-12}$, normal or branched, alkane. The inert hydrocarbon may be halogenated, but preferably is not. More preferably still, the inert hydrocarbon utilized is hexane, isooctane, n-octane or hydrogenated propylene tetramer, and most preferably, isooctane is used. The mixture resulting from addition of the inert hydrocarbon to the reaction product is then heated at a temperature and pressure whereby the mixture is caused to reflux. When isooctane is used, the mixture is heated in the temperature range of about 99°–25° C. at atmospheric pressure. In addition to monomer or feedstock, dimer ester and the desired trimer ester, the reaction product includes the $BF_3$ complex of the monomer, as well as the $BF_3$ complex of the trimer ester. Heating the mixture to reflux causes these complexes to thermally dissociate, thereby releasing gaseous $BF_3$. The vaporized solvent is condensed and returned to the reaction vessel while the gaseous $BF_3$ passes through the condenser and is recovered for reuse. The $BF_3$ may be compressed for storage or immediate reuse. However, the $BF_3$ losses associated with gas compression and storage may be conveniently avoided by complexing the $BF_3$ with additional feedstock ester. This resulting complexed ester may be stored for later use or used immediately, as in a continuous-type industrial operation, to continue the present process. For efficient and economical $BF_3$ recovery, solvent refluxing is advantageous compared to known solvent stripping procedures for several reasons. Solvent stripping requires heating the reaction product with little or no solvent dilution. This was found to cause degradation of the reaction product by anhydride formation as well as to decrease $BF_3$ recovery by causing the formation of difficult to dissociate $BF_3$-alcohol complexes. Also, the solvent refluxing method requires less equipment and the use of substantially smaller quantities of solvent than does stripping.

Following $BF_3$ removal, the reaction product may be further treated by known methods to obtain the desired trimer acid therefrom. The inert hydrocarbon solvent is removed from the reaction product by methods such as distillation, stripping or flash evaporation. The reaction product at this point is chiefly a mixture of trimer ester, dimer ester, and unreacted monomer. The reaction product is washed with water to remove any residual $BF_3$. The esters are then hydrolyzed to the corresponding acids by known procedures including both pressure splitting, Twitchell hydrolysis, and high-temperature steam sparging. The steam sparging method was found to be the most efficient of the three. Batch pressure-splitting was found to be tedious in a sample run using a methyl ester feedstock because the methanol resulting from hydrolysis was soluble in the organic phase, requiring up to seven splits to complete hydrolysis of a given batch. The desired trimer acid may then be purified by methods such as molecular distillation.

The present invention will be further described in the following Examples, which are not to be construed as limiting the invention in any respect. In the Examples, all percentages are on a weight basis unless otherwise indicated.

EXAMPLE 1

A 250 ml 4-necked round bottom glass flask was fitted with a thermometer, $BF_3$ inlet tube, a septum for sampling, a condenser and a mechanical stirrer. The top of the condenser was connected to a small trap containing NaOH (KOH) to neutralize the evolved BF3. $BF_3$ was supplied via the inlet tube from a commercially available pressurized steel cylinder and was protected against accidental backflow of the reaction flask contents by a small trap. The flask was charged with 150 g of tall oil methyl ester, having an acid value of 5.72, and cooled in a water/ice bath. $BF_3$ was bubbled into the ester with stirring, resulting in the evolution of heat.

The reaction temperature of 25° C. was maintained, by regulation of the $BF_3$ flow rate and use of the water/ice bath, with stirring for 3.0h. The reaction pressure was maintained at 2 in. of $H_2O$ pressure by adjusting the depth of the $BF_3$ exhaust tube in the caustic trap. It should be noted that the process has been conducted at pressures of up to about 50 psi without any apparent effect on product yield or distribution, or $BF_3$ recovery yield. After 3.0h, as shown in Table I (Sample No. 134), thermal gravimetric analysis (TGA) revealed that the reaction product contained 21.5 w/o unreacted monomer, 24.5 w/o dimer, and 54 w/o trimer and higher. 300 g of isooctane were then introduced into the flask with stirring. The resulting mixture was brought to reflux temperature and allowed to reflux for 120 min. During this time BF3 was evolved and trapped in caustic. Atomic absorption spectroscopy of the boron content of initial (before reflux) and final (after reflux) samples of the reaction mixture revealed a 90.4 w/o removal of $BF_3$ after refluxing for 120 min.

EXAMPLE 2

A continuous 3-stage overflow reactor was constructed by connecting two 1L 4-necked glass sidearm flasks (the first and second flasks) and a 500 mL flask of the same type (the third flask) in series using the sidearms to provide for overflow from the first flask to the second, and from the second to the third by means of gravity. Each flask was fitted with a thermometer, a $BF_3$ inlet tube, a mechanical stirrer and a water/ice bath in the manner described in Example 1. The sidearm of the third flask emptied into a receiver which was vented via a dry trap and a caustic trap. The procedure of Example 1 was modified in readily understood ways to accomodate use of the continuous apparatus. The reactor flasks were cooled by the water/ice baths and the reactor was charged with methyl soyate (the methyl esters of the mixture of fatty acids derived from soybean oil), having an acid value of 8.95, at a flow rate of 1000 grams per hour (g/h). A total of 1000 g of methyl soyate was used. $BF_3$ was bubbled into each of the three flasks with stirring, resulting in the evolution of heat. The residence time of the reaction mixture in the first and second flasks was about 1 h each, and that in the third flask was about 0.5 h, during which the reaction temperature was maintained at about 25° C. As shown in Table I (Sample No. 37), TGA revealed that the reaction product was composed chiefly of 25 w/o monomer, 22 w/o dimer, and 53 w/o trimer. After refluxing in 2000 g of isooctane for 240 min, atomic absorption spectroscopy indicated a 93.7 w/o removal of $BF_3$.

EXAMPLE 3

Using essentially the same apparatus and procedure as described in Example 1, 150 g of methyl soyate, having an acid value of 0.4, were reacted with $BF_3$ for about 3.0h at about 20°–25° C. under 2 in. of $H_2O$ pressure. As shown in Table I (Sample No. 43), after 3.0H, TGA revealed that the reaction product included 32 w/o monomer, 19 w/o dimer, and 49 w/o trimer or higher. The reaction product was mixed with 300 g of isooctane and refluxed for 60 min, resulting in a 99.5 w/o removal of $BF_3$ as measured by atomic absorption spectroscopic analysis for boron.

The terms and expressions which have been employed herein are used as terms of description and not of limitation, and there is no intention in the use of such terms and expressions of excluding any equivalents of the features shown and described, or portions thereof, but it is recognized that various modifications are possible within the scope of the invention claimed.

TABLE 1

| Sample No. | Feedstock | Starting Acid Value | w/o Monomer | w/o Dimer | w/o Trimer or Higher | Reflux Solvent | Reflux Time (min.) | w/o Boron Removed |
|---|---|---|---|---|---|---|---|---|
| 119 | Tall Oil Methyl Ester | 5.72 | 19 | 26 | 55 | Hexane | 120 | 75.0 |
| 120 | Tall Oil Methyl Ester | " | 19 | 26 | 55 | " | 210 | 88.2 |
| 125 | Tall Oil Methyl Ester | " | 19 | 26 | 55 | " | 120 | 87.8 |
| 139 | Tall Oil Methyl Ester | " | 28 | 22 | 50 | " | 60 | 88.2 |
| 134 | Tall Oil Methyl Ester | " | 21.5 | 24.5 | 54 | Isooctane | 120 | 90.4 |
| 143 | Tall Oil Methyl Ester | " | 23 | 26 | 51 | " | 120 | 90.2 |
| 22 | Tall Oil Methyl Ester | " | 32 | 19 | 49 | HPT[1] | 60 | 86.5 |
| 37 | Methyl Soyate | 8.95 | 25 | 22 | 53 | Isooctane | 240 | 93.7 |
| 43 | Methyl Soyate | 0.4 | 32 | 19 | 49 | " | 60 | 99.5 |
| 44 | Methyl Soyate | " | 33 | 18 | 49 | " | 60 | 99.4 |

[1]HPT = Hydrogenated Propylene Tetramer

What is claimed is:

1. A process for preparing an oligomer of at least one polyunsaturated aliphatic $C_{12-22}$ monocarboxylic acid ester in the presence of boron trifluoride, and for recovering said boron trifluoride, comprising the steps of:
   (a) reacting at least one said ester, having an acid value of about 0.01-10, at a reaction temperature and for a time sufficient to produce a predominantly trimeric reaction product;
   (b) mixing an inert hydrocarbon having a boiling point of 50° C. or higher with said reaction product;
   (c) heating the resulting mixture at a temperature causing said mixture to reflux, thereby releasing gaseous boron trifluoride; and
   (d) recovering at least the major portion of said boron trifluoride.

2. A process as recited in claim 1 wherein said reaction temperature is about 0°–100° C.

3. A process as recited in claim 1 wherein said reaction temperature is about 20°–40° C.

4. A process as recited in claim 1 wherein said acid value is about 0.01-6 and at least about 85 w/o of said boron trifluoride is recovered.

5. A process as recited in claim 4 wherein said acid value is about 0.01-1.5 and said recovery of said boron trifluoride is essentially quantitative.

6. A process as recited in claim 1 wherein said reaction temperature is about 20°-40° C., said acid value is about 0.01-1.5, and said recovery of boron trifluoride is essentially quantitative.

7. A process as recited in claim 1 wherein said inert hydrocarbon is a $C_{6-12}$, normal or branched, alkane.

8. A process as recited in claim 7 wherein said inert hydrocarbon is selected from the group consisting of hexane, n-octane, isooctane and hydrogenated propylene tetramer.

9. A process as recited in claim 8 wherein said inert hydrocarbon is isooctane.

10. A process as recited in claim 1 wherein said ester is a $C_{1-20}$ alkyl ester of said monocarboxylic acid.

11. A process as recited in claim 10 wherein said alkyl group is selected from the group consisting of methyl, ethyl and propyl.

12. A process as recited in claim 11 wherein said alkyl group is methyl.

13. A process as recited in claim 1 wherein an oil-derived ester is reacted, said ester being derived from an oil selected from the group consisting of soybean oil, sunflower oil, corn oil, and cottonseed oil.

14. A process for preparing an oligomer of at least one polyunsaturated aliphatic $C_{12-22}$ monocarboxylic acid methyl ester in the presence of > boron trifluoride, said methyl ester being selected from a group consisting of methyl esters of soybean oil, methyl esters of sunflower oil, methyl esters of corn oil and methyl esters of cottonseed oil, said process comprising the steps of:

(a) reacting at least one said methyl ester, having an acid value of about 0.01-1.5, at a reaction temperature of about 20-40° C. to produce a predominantly trimeric reaction product;

(b) mixing isooctane with said reaction product;

(c) heating said mixture at a temperature from about 99° to about 125° C., at atmospheric pressure, thereby releasing gaseous boron trifluoride; and (d) recovering an essentially quantitative amount of said boron trifluoride.

* * * * *